United States Patent [19]

Armington

[11] Patent Number: 4,934,376
[45] Date of Patent: Jun. 19, 1990

[54] METHOD AND APPARATUS FOR DETECTING HEARTBEATS

[75] Inventor: Robert M. Armington, West Peabody, Mass.

[73] Assignee: Siemens Medical Electronics, Inc., Danvers, Mass.

[21] Appl. No.: 205,409

[22] Filed: Jun. 10, 1988

[51] Int. Cl.⁵ .............................................. A61N 1/00
[52] U.S. Cl. .................................... 128/696; 128/695; 128/697
[58] Field of Search ............... 128/696, 697, 704, 706, 128/708, 695, 419 PT, 419 PG

[56] References Cited

U.S. PATENT DOCUMENTS

| | | | |
|---|---|---|---|
| 4,105,023 | 8/1978 | Marchese et al. | 128/697 |
| 4,476,869 | 10/1984 | Bihn | 128/418 PT |
| 4,537,201 | 8/1985 | Delle-Vedove et al. | 128/708 |
| 4,791,936 | 12/1988 | Snell et al. | 128/419 PT |

*Primary Examiner*—Francis Jaworski
*Assistant Examiner*—George Manuel
*Attorney, Agent, or Firm*—Lawrence C. Edelman

[57] ABSTRACT

Method and apparatus for detecting the occurrence of heartbeats in an ECG signal which may also include pacer artifacts, comprising analysis of the ECG signal for providing a heartbeat signal indicating detection of the occurrence of a heartbeat, analysis of the ECG signal for providing a pacer artifact signal indicating detection of the occurrence of a pacer artifact, analysis of the ECG signal in a manner independent from the first-mentioned analysis for determining if a portion of the ECG signal which follows detection of a pacer artifact has changes in its amplitude level which indicate the validity of the heartbeat indicating signal, and use of the result of the last-mentioned analysis to control the providing of the heartbeat indicating signal by the first-mentioned analysis.

21 Claims, 4 Drawing Sheets

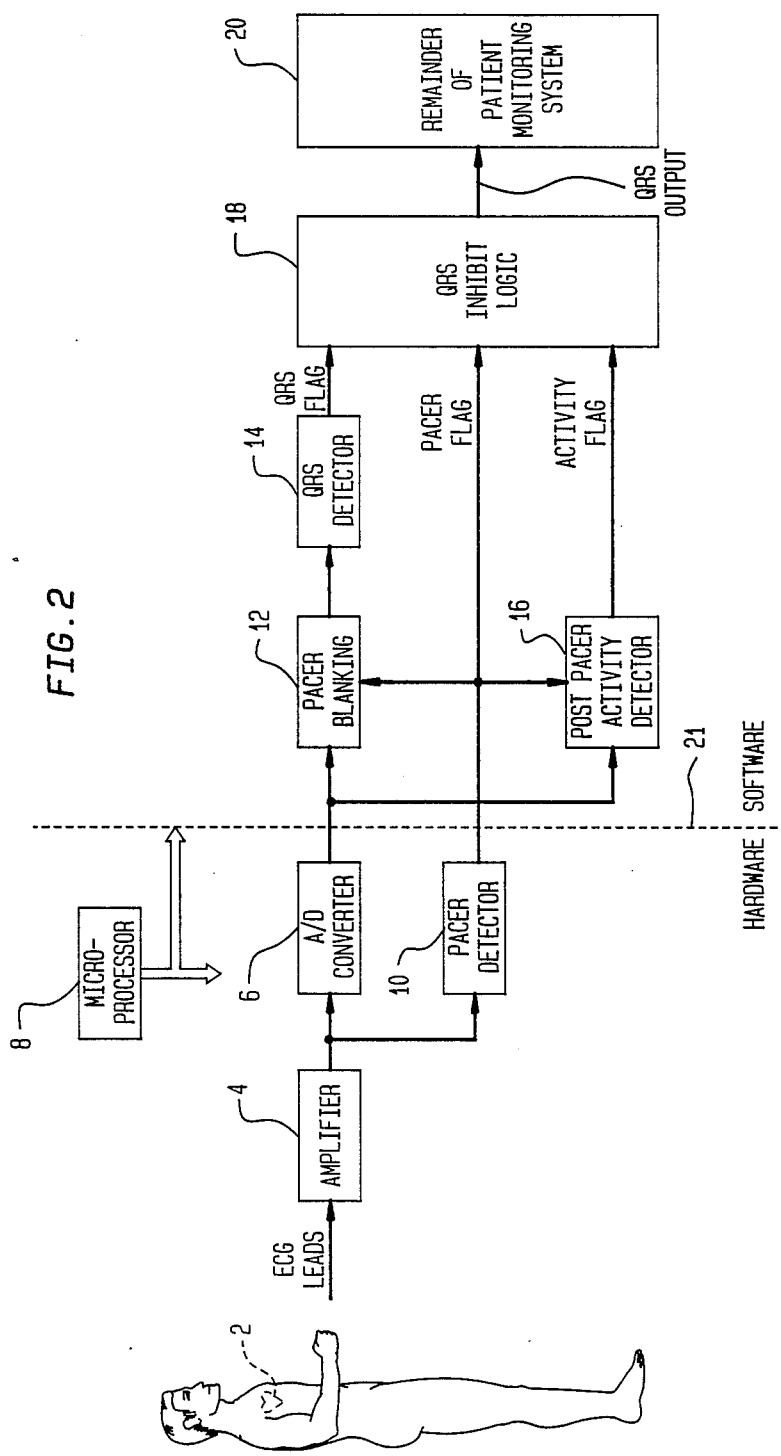

METHOD AND APPARATUS FOR DETECTING HEARTBEATS

BACKGROUND OF THE INVENTION

1. Field of the Invention

The present invention relates to a method and apparatus for detecting heartbeats, and more particularly, to means for preventing pacemaker artifacts from being erroneously detected as QRS complexes.

2. Description of the Prior Art

Establishing the condition of the heart of a patient is typically accomplished by monitoring its electrical activity. Patient monitoring systems develop and analyze ECG signals which are responsive to the electrical activity of the heart. One type of analysis carried out by a patient monitoring system is to detect the QRS complex portions of the ECG signals, whose output is used to measure heartrate. QRS detectors typically comprise an amplitude or slew-rate detector since the QRS complex is normally both the fastest rising and largest amplitude (typically 0.25-2 millivolts) component of a normal ECG signal. However, this is not always true. For example, in the case of a patient having a pacemaker, the pacer signals (artifacts including an impulse of typically 2-700 millivolts) may be either erroneously detected as a QRS complex or may so disrupt the QRS detector that it will not be able to properly function. Since persons with pacemakers are a class of people for which patient monitoring is extremely important, it is critical that QRS complexes, as well as other portions of the ECG signals are properly analyzed by the patient monitoring system and are not disrupted or "fooled" by the pacer artifacts so that accurate heartrates can be measured.

Accordingly, patient monitors typically contain circuitry for detecting pacemaker artifacts. The output of this detector is used by the QRS detector to identify what portion of the incoming ECG data contains the pacemaker artifact. A common technique used in QRS detection is to remove or blank the ECG data corresponding to the pacer artifact before it is processed by the QRS detector. An example of this technique is shown in the idealized ECG signal illustrated in FIGS. 1a and 1b.

FIGS. 1c and d illustrate examples of an ECG signal before and after pacer impulse blanking, respectively, which signal has a relatively large repolarization tail and no subsequent heart activity. Unfortunately, the above described technique does not work well during this situation because that portion of the artifact which remains after blanking may be large enough to be detected by a typical QRS detector. Increasing the amount of ECG data being blanked is not a practical solution because if a QRS complex occurred during the time that the ECG data is blanked, it would be missed by the detector.

In another technique, the QRS detector algorithm reduces the sensitivity of the QRS detector during the time immediately following detection of a pacer artifact. Although this may improve the performance of the detector in the presence of large pacer artifacts, it may also cause low-amplitude QRS complexes to be missed by the detector.

Accordingly, it is an object of the present invention to provide a method and apparatus which will allow for the accurate detection of QRS complexes in the presence of pacer artifacts.

SUMMARY OF THE INVENTION

In accordance with the principles of the present invention a method and apparatus is provided for detecting a predetermined portion of an ECG signal, such as the QRS complex, in the presence of interfering pacer artifacts. In its broadest aspect, the invention comprises inhibiting the output of a detector which detects a portion of the ECG signal (such as the QRS complex) if the shape (i.e., changing amplitude levels) of that portion of the ECG signal following a pacer artifact does not deviate from the shape expected for that portion when no cardiac response to the pacer artifact is present.

More specifically, if a QRS detection occurs during the time interval that a QRS complex would be expected to occur in response to a pacer impulse, yet no significant electrical activity is detected by a post pacer activity detector, the output of the QRS detector is inhibited. This is accomplished by means of a post pacer activity detector which receives the ECG signal in parallel with the input of the QRS detector and accumulates amplitude changes of successive samples of the ECG signal which are opposite in polarity to those which would be expected during a pacer repolarization tail in the absence of heart activity. If a pacer artifact is detected, the QRS detector output is inhibited unless the sum of the opposite polarity amplitude changes during a predetermined time interval exceeds a given threshold level. Accordingly, in the presence of pacer artifacts, the QRS detector is not enabled to provide an output until an independent analysis has been performed on the ECG signal which indicates that significant heart activity exists.

In accordance with a further feature of the invention, the amplitude threshold level used by the activity detector is adjustable in direct response to the amplitude of the pacer tail.

Other features and advantages of the invention will be apparent from the description of the preferred embodiment and from the claims.

For a fuller understanding of the present invention, reference should now be made to the following detailed description of the preferred embodiment of the invention and to the accompanying drawings.

BRIEF DESCRIPTION OF THE DRAWING

FIG. 2 illustrates in functional block diagram form a patient monitoring system including a QRS detector arrangement constructed in accordance with the principles of the present invention;

DETAILED DESCRIPTION OF THE PREFERRED EMBODIMENT

Figure 1A:
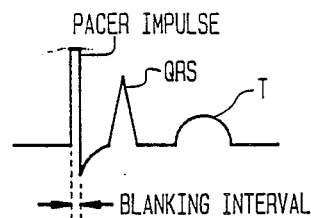
FIGS. 1a, b, c and d, previously referred to, illustrate ECG waveforms useful for understanding the previously described state of the art.
Figure 1B:
Figure 1C:
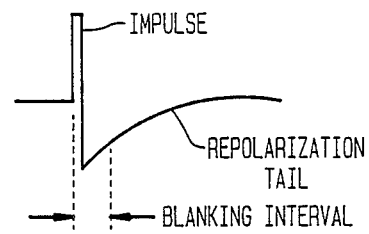
Figure 1D:

Referring to FIG. 2, electrical signals generated by expansion and contraction of the heart 2 of a patient, as well as pacer artifact signals generated by a pacemaker (not shown), are coupled by ECG leads to a conventional ECG amplifier 4. ECG amplifier 4 filters, amplifies and combines the electrical signals sensed by the ECG leads and generates at its output a time-varying signal representative of the electrical activity of heart 2. FIG. 1a is illustrative of the signal at the output of amplifier 4.

Figure 3A:
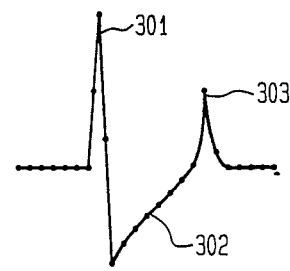
FIGS. 3a, b and c illustrate signal waveforms at various portions of the FIG. 2 arrangement.

In a conventional manner, an analog-to-digital (A/D) converter 6 samples the ECG signal provided from amplifier 4 at a rate defined by a sampling signal (not shown) provided from a microprocessor controller 8. FIG. 3a illustrates a portion of the output of A/D converter 6 during a time period which includes a pacer impulse 301 and its repolarization tail 302. A QRS complex 303 is also shown. A pacer detector 10 also receives the ECG signal provided at the output of amplifier 4 and sets a pacer flag upon detection of the Pacer artifact. Pacer detector 10 may comprise a slew rate detector such as described by Thomas A. Mans in his U.S. Pat. No. 4,539,999.

Figure 3B:
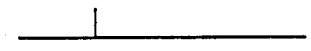
Figure 3C:
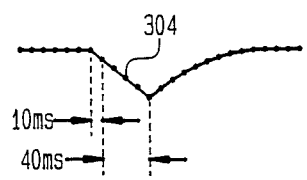

The digitized ECG signal at the output of A/D converter 6 is divided into two parallel paths. In a first path, a pacer blanker 12 applies the digitized ECG signal to a QRS detector 14, of conventional design, which sets a QRS flag upon detection of a QRS complex. Although not shown, a delay is included in the first path in order to allow completion of ECG signal processing in the second path. Pacer blanker 12 is responsive to the pacer flag generated by pacer detector 10 for controllably blanking the pacer impulse of the ECG signal, as well as a portion of its repolarization tail. As illustrated by FIGS. 3b and c, pacer blanker 12 blanks the ECG signal from 10 milliseconds before impulse 301 to 40 milliseconds after impulse 301 and calculates and substitutes therefore a linearly sloped portion 304. This blanking time is kept to a minimum so that closely coupled QRS complexes are not normally affected. It should be noted that pacer blanker 12 is included in the preferred embodiment because the presence of large pacer impulses can effect the sensitivity of QRS detector 14 since it normally has an adjustable threshold level. However, other types of QRS detectors may be less sensitive to large pacer impulses, thereby obviating the need for a pacer blanker. In the parallel path, the digitized ECG signal is applied to a post pacer activity detector 16. Activity detector 16 provides an analysis which is independent of the analysis performed by QRS detector 14 for qualifying the output of detector 14, i.e., by determining if there is significant cardiac activity following a pacer impulse. Significant cardiac activity is defined as ECG signal levels which deviate a prescribed amount from those levels expected when there is no cardiac response to a pacer impulse. Upon indication of significant cardiac activity, an activity flag is set and applied to a QRS inhibit logic 18. QRS inhibit logic 18 is also responsive to the pacer flag and the QRS flag and prevents the remaining portion of the patient monitoring system from receiving the set QRS flag if a pacer artifact was detected at an appropriate interval before the QRS flag is set and no significant cardiac activity is found following the pacer impulse. Alternatively stated, if either the pacer flag is not set or the pacer flag is set and the activity flag is also set during a predetermined time interval, the QRS output is not inhibited. If, for example, the patient does not have a pacemaker, the pacer flag is not set and therefore the QRS inhibit logic will not operate to inhibit the passage of a set QRS flag, which indicates detection of a QRS complex to a heartrate calculating device (not shown) included in the remaining portion 20 of the patient monitoring system. Further details of this operation will be described in conjunction with the flow charts of FIGS. 4 and 5.

In the preferred embodiment of the patient monitoring system shown in FIG. 2, that portion illustrated to the left of dotted line 21 is based in hardware and that portion illustrated to the right of dotted line 21 is based in software and controlled by microprocessor 8.

Figure 4:
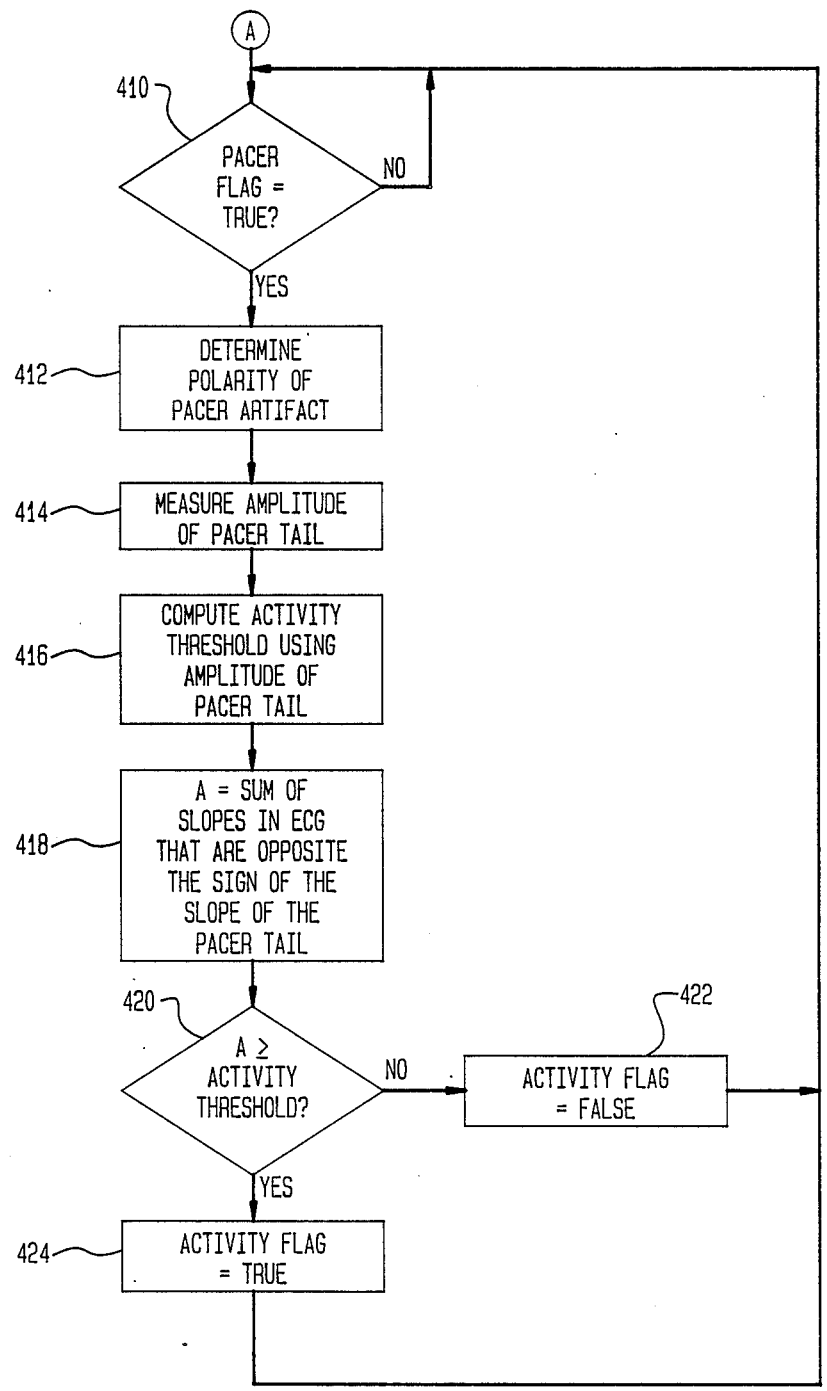
FIG. 4 illustrates a flow chart of the operation of the post pacer activity detector shown in FIG. 2.

FIG. 4 illustrates a flow chart of the operation algorithm of activity detector 16. In step 410 the setting by pacer detector 10 of the pacer flag to true is detected. If the pacer flag is true, step 412 determines the polarity of the pacer impulse. This can be accomplished by detecting the amplitude change of successive-in-time samples of the ECG signal (such as the ECG signal illustrated by FIG. 3a which has a positive polarity impulse). Step 414 measures the ECG signal amplitude at the beginning of the pacer tail, i.e., that amplitude difference between the base line of FIG. 3a and the beginning of repolarization tail 302. Step 416 computes the activity threshold amplitude level for activity detector 16 in direct response to the amplitude level of the pacer tail measured in step 414. Step 418 calculates the slope of the successive-in-time samples of the ECG signal and accumulates the amplitude changes of those slopes which have an opposite polarity to the polarity determined by step 412 (i.e., a negative polarity, such as shown for the right side of the QRS complex portion 303 in FIG. 3a). If the accumulated amplitude changes of the opposite polarity slopes does not exceed the adjustable threshold amplitude level set by step 416, activity detector 16 sets the activity flag false, via step 422 and the program returns to point A. If, however, step 420 determines that the amplitude calculated in step 418 exceeds the activity threshold determined from step 416, step 424 causes the activity flag to be set true and the algorithm returns to point A wherein the next operating cycle of activity detector 16 is repeated.

Figure 5:
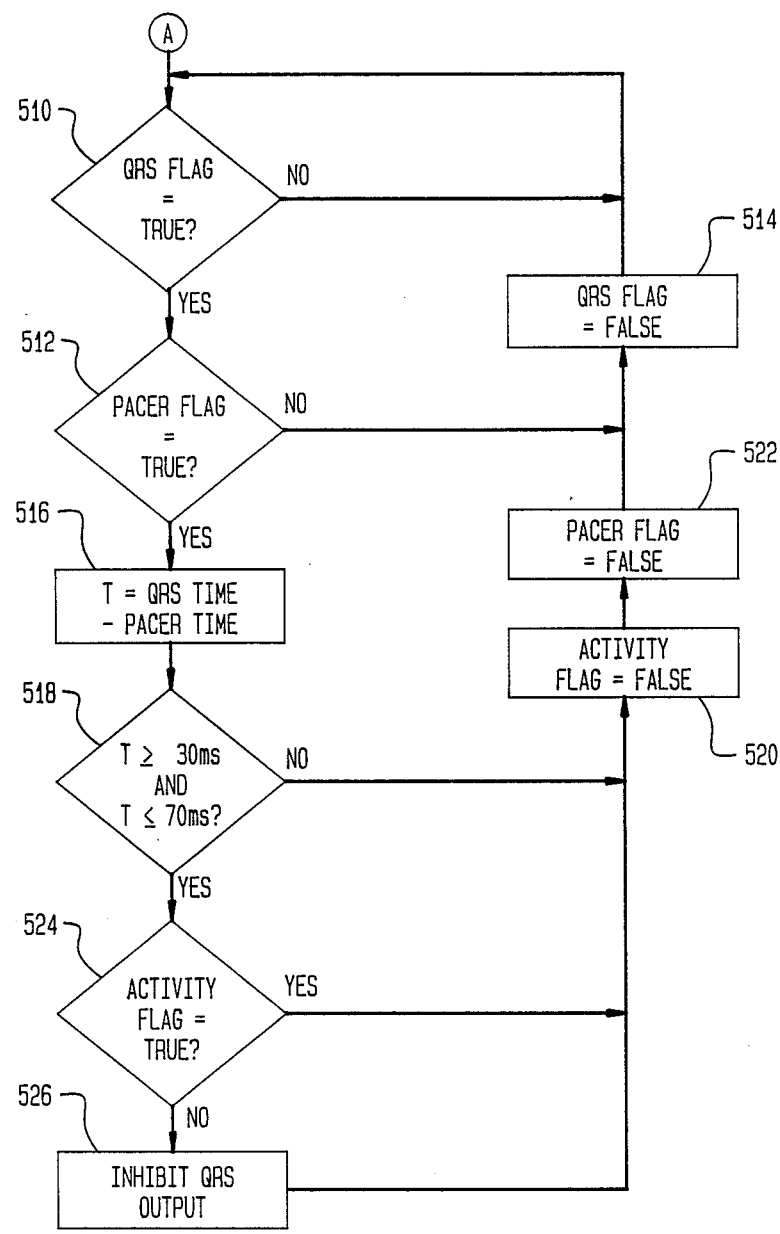
FIG. 5 illustrates a flow chart of the operation of the QRS inhibit logic shown in FIG. 2.

The activity flag as well as the pacer flag and the QRS flag are used by the QRS inhibit logic 18 in a manner illustrated in conjunction with the flow chart of FIG. 5. FIG. 5 illustrates a flow chart of the operation algorithm of QRS inhibit logic 18. In step 510 the setting by QRS detector 14 of the QRS flag to true is detected and in step 512 the setting by pacer detector 10 of the pacer flag to true is detected. If the pacer flag is not set true, step 514 resets the QRS flag to false. If, however both flags are true, step 516 calculates the time interval between the setting of the QRS flag to true and the setting of the pacer flag to true. Step 518 determines if the calculated time interval is within the range between 30 and 70 milliseconds (i.e., the range expected for the occurrence of a QRS complex generated by the heart in response to a pacer impulse). If the calculated time interval is not within this range, steps 520, 522 and 514 reset the activity, pacer and QRS flags, respectively, to false and the above process is repeated. However, if the calculated time interval is within this range, step 524 determines if the activity flag has also been set to true and, if not, step 526 inhibits the QRS output (i.e. the set QRS flag) since it has been determined that significant cardiac activity following a pacer artifact has not been found. On the other hand, if the activity flag was set true by activity detector 16 during this time interval, thereby indicating significant cardiac activity following a pacer artifact, then the set QRS flag is not inhibited by inhibit logic 18 and is received as an input to a heartrate calculating device (not shown) included in the remainder 20 of the patient monitoring system. In either case, all flags are then set to false by steps 514, 520 and 522 and the above process is repeated.

Thus, there has been shown and described novel apparatus for reliably detecting a portion of an ECG signal (such as a QRS complex) in the presence of pacemaker artifacts. Many changes, modifications, variations and other uses and applications of the subject invention will, however, become apparent to those skilled in the art after considering this specification and the accompanying drawings, which disclose a preferred embodiment thereof. For example, the inventive method and apparatus could be used for detecting other portions of the ECG signal. Additionally, it is not necessary that the amplitude threshold level of the activity detector be adjustable. Furthermore, as noted in the specification, the pacer blanker may not be necessary, depending upon the design of the QRS detector and furthermore the time periods noted in the preferred embodiment could be modified. Additionally, the post pacer activity detector could be differently implemented. For example, it could analyze the ECG signal following the pacer impulse by looking for amplitude changes which deviate from the expected exponential decay of a pacer repolarization tail. All such changes, modifications, variations and other uses and applications which do not depart from the spirit and scope of the invention are deemed to be covered by the invention which is limited only by the claims which follow.

What I claim is:

1. A method for detecting the occurrence of heartbeats in an ECG signal which may also include pacer artifacts, comprising the following steps:
   analyzing the ECG signal and providing a heartbeat signal upon detection of the occurrence of a heartbeat;
   analyzing the ECG signal and providing a pacer artifact signal upon detection of the occurrence of a pacer artifact;
   analyzing the ECG signal and determining if a portion of the ECG signal which follows detection of a pacer artifact has a shape which indicates the validity of the heartbeat signal; and
   using the result of said last-mentioned analysis step to control the providing of said heartbeat signal by said first-mentioned analyzing step.

2. The method according to claim 1, wherein:
   said last-mentioned analyzing step is responsive to the heartbeat and pacer artifact signals for determining if the shape of a portion of the ECG signal which follows said pacer artifact signal deviates a significant amount from an expected shape for that portion.

3. The method according to claim 2, wherein, said expected shape in that shape for an ECG signal when there is substantially no heart activity following a pacer artifact.

4. The method according to claim 3, wherein:
   said using step inhibits the providing of said heartbeat signal when the shape of said portion of said ECG signal does not substantially deviate from said expected shape.

5. The method according to claim 1, wherein:
   said first-mentioned analyzing step comprises analyzing said ECG signal and indicating the detection of the occurrence of a QRS complex.

6. The method according to claim 5, wherein:
said last-mentioned analyzing step analyzes said ECG signal during a time period which includes 30 milliseconds to 70 milliseconds after occurrence of said pacer artifact signal.

7. A method for deriving a heartrate signal by detecting the occurrence of heartbeats in an ECG signal which may also include pacer artifacts, comprising the following steps:
   analyzing the ECG signal and providing a heartbeat signal upon detection of the occurrence of the QRS complex;
   analyzing the ECG signal and providing a pacer artifact signal upon detection of the occurrence of a pacer impulse;
   analyzing the ECG signal and determining if a portion of the ECG signal which follows detection of a pacer impulse has changes in its amplitude level which indicate the validity of the heartbeat signal; and
   using the result of said last-mentioned analysis step to control the providing of said heartbeat signal to a heartrate calculating device.

8. The method according to claim 7, wherein:
   said last-mentioned analyzing step is responsive to said heartbeat and pacer artifact signals for inhibiting use of said heartbeat signal by said heartrate calculating device if the shape of a portion of the ECG signal which follows said pacer artifact signal does not deviate a significant amount from a shape expected for that portion when no heart activity is generated in response to the pacer artifact.

9. Apparatus for detecting the occurrence of heartbeats in an ECG signal which may also include pacer artifacts, comprising:
   means for analyzing the ECG signal and providing a heartbeat signal upon detection of the occurrence of a heartbeat;
   means for analyzing the ECG signal and providing a pacer artifact signal upon detection of the occurrence of a pacer artifact;
   activity detector means for analyzing the ECG signal and determining if a portion of the ECG signal which follows detection of a pacer artifact has changes in its amplitude level which exceed a predetermined threshold level, thereby indicating the validity of the heartbeat signal, and providing an activity indicating signal in response to said determination; and
   means for using the activity indicating signal to control the providing of said heartbeat signal by said first-mentioned analyzing means.

10. Apparatus according to claim 9, wherein:
    said activity detector means is responsive to the ECG signal and pacer artifact signal for evaluating the shape of a portion of the ECG signal which follows the occurrence of said pacer artifact signal.

11. Apparatus according to claim 10, wherein:
    said activity detector means includes an amplitude detector for detecting amplitude changes of said ECG signal, a summing means for summing detected amplitude changes of said ECG signal and a threshold circuit responsive to a sum of the detected amplitude changes.

12. Apparatus according to claim 11, wherein:
    said activity detector means determines that said heartbeat signal is valid in response to an indication from said threshold circuit that the sum of the ECG signal detected amplitude changes have exceeded a predetermined threshold level during a predetermined time period.

13. Apparatus according to claim 11, wherein:
said activity detector means determines that said heartbeat signal is not valid in response to an indication from said threshold circuit that the sum of the ECG signal detected amplitude changes have not exceeded a predetermined threshold level during a predetermined time period.

14. Apparatus according to claim 12, wherein:
said predetermined threshold level is determined in response to the amplitude of said ECG signal at the beginning of a pacer artifact repolarization tail.

15. Apparatus according to claim 13, wherein:
said predetermined threshold level is determined in response to the amplitude of said ECG signal at the beginning of a pacer artifact repolarization tail.

16. Apparatus according to claim 11, wherein:
said second-mentioned analyzing means also includes means for indicating the polarity of detected pacer artifacts in said ECG signal; and
said summing means only sums detected amplitude changes in a portion of said ECG signal which follows a detected pacer artifact and which are opposite in polarity form the polarity of the detected pacer artifact.

17. Apparatus for detecting the occurrence of heartbeats in an ECG signal which may also include pacer artifacts, comprising:
a QRS detector for analyzing the ECG signal in a first signal processing path and providing a QRS detection signal upon detection of a QRS signal complex occurring in said ECG signal;
a pacer artifact detector for analyzing the ECG signal and providing a pacer artifact detection signal upon detection of a pacer artifact occurring in said ECG signal;
an activity detector means for analyzing the ECG signal in a second signal processing path which is parallel with said first signal processing path for determining if a portion of the ECG signal which follows detection of a pacer artifact has amplitude level changes which exceed a predetermined threshold level, thereby indicating validity of the QRS detection signal, and providing an activity indicating signal in response to said determination; and
means for using said activity indicating signal to control the providing of said QRS detection signal to a utilization means.

18. Apparatus according to claim 17, wherein:
said activity detector means includes an amplitude detector for detecting changes in amplitude of said ECG signal, a summing means for summing the detected amplitude changes and a threshold circuit responsive to sum of the detected amplitude changes, the output of said threshold circuit providing said activity indicating signal.

19. Apparatus according to claim 18, wherein:
said activity detector means includes comparing means for providing said activity indicating signal when said threshold circuit has summed ECG signal detected amplitude changes which exceed a predetermined threshold level during a predetermined time period.

20. Apparatus according to claim 19, wherein:
said predetermined threshold level is determined in response to the amplitude of said ECG signal at the beginning of a pacer artifact repolarization tail.

21. Apparatus according to claim 18, wherein:
said pacer artifact detector includes means for indicating the polarity of detected pacer artifacts; and
said summing means is enabled by said pacer artifact detection signal so as to only sum detected amplitude changes in a portion of said ECG signal which follows a detected pacer artifact and which are opposite in polarity from the polarity indicated for said detected pacer artifact.

* * * * *